United States Patent [19]

Hokanson et al.

[11] Patent Number: 4,680,416

[45] Date of Patent: Jul. 14, 1987

[54] ANTIBIOTIC CL-1565 COMPLEX DERIVATIVES

[75] Inventors: Gerard C. Hokanson; Richard H. Bunge; Timothy R. Hurley; James C. French, all of Ann Arbor, Mich.

[73] Assignee: Warner-Lambert Company, Morris Plains, N.J.

[21] Appl. No.: 755,389

[22] Filed: Jul. 16, 1985

Related U.S. Application Data

[63] Continuation of Ser. No. 493,888, May 12, 1983, abandoned.

[51] Int. Cl.$^4$ .............................................. C07D 309/32
[52] U.S. Cl. ..................................... 549/292; 549/294
[58] Field of Search ................................ 549/294, 292

Primary Examiner—Norma S. Milestone
Attorney, Agent, or Firm—Jerry F. Janssen

[57] ABSTRACT

Novel pyranone compounds and related compounds, methods of preparing the compounds, and their use as cytotoxic and/or antileukemic agents or precursors, are provided.

3 Claims, No Drawings

ANTIBIOTIC CL-1565 COMPLEX DERIVATIVES

This is a continuation of application Ser. No. 493,888, filed May 12, 1983, now abandoned.

Phosphorus containing antibiotic compounds designated CL 1565-A, CL 1565-B, and CL 1565-T which, for purposes of the present invention are useful as starting materials and are referred to hereinafter, are described in detail in U.S. Pat. No. 4,578,383 issued Mar. 25, 1986 which derived from application Ser. No. 627,367 which was a continuation-in-part of application Ser. No. 447,544 filed Dec. 7, 1982 (now abandoned) which, in turn, is a continuation-in-part of Ser. No. 439,973 filed Nov. 8, 1982 (now abandoned) which, in turn, is a continuation-in-part of application Ser. No. 351,704 filed Feb. 24, 1982 (now abandoned). The applications are commonly owned with the present application, and their subject matter is incorporated herein by reference.

SUMMARY AND DETAILED DESCRIPTION

The present invention in one preferred embodiment relates to novel pyranones, particularly 5,6-dihydro-2H-pyran-2-one compounds and related compounds, methods of preparing the compounds, and their use as cytotoxic and/or antileukemic agents or precursors. Thus, the invention in one aspect relates to compounds in substantially pure form, as follows:

a. Alcohols having the structural formulas 1a, 1b, and 1c:

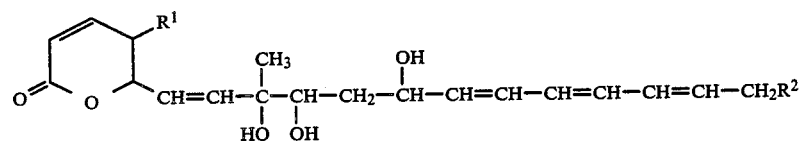

1a, $R^1=H$; $R^2=OH$
1b, $R^1=R^2=H$
1c, $R^1=R^2=OH$ b. phosphates, preferably as their sodium salts or other salts, having the structural formulas 2a, 2b, and 2c:

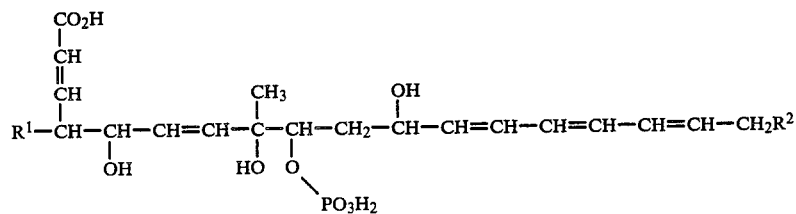

2a, $R^1=H$; $R^2=OH$
2b, $R^1=R^2=H$
2c, $R^1=R^2=OH$ c. lower alkyl or aryl esters of the phosphate function of said phosphates of b and of the phosphate function of the above mentioned CL 1565-A, CL 1565-B, and CL 1565-T, having the structural formulas 3a, 3b, and 3c, respectively:

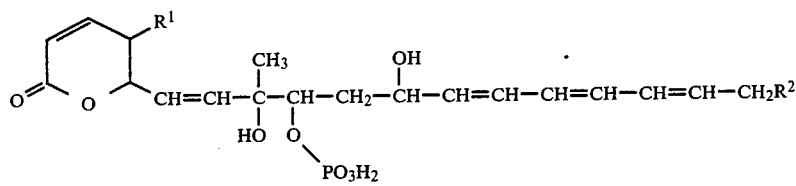

3a $R^1=H$; $R^2=OH$
3b $R^1=R^2=H$
3c $R^1=R^2=OH$ d. acyl esters of said alcohols of a, said salts of said phosphate esters of b, said phosphate esters of c, and of the salts, preferably sodium salts, of compounds 3a, 3b, and 3c;

e. the compound designated CL 1565-PT-3; and f. pharmaceutically acceptable forms of said alcohols of a; said phosphates of b; said esters of c; said acyl esters of d; and said CL 1565-PT-3.

The term acyl as used herein refers to acyl groups of acids that may be straight chain, branch chain, substituted saturated, unsaturated, or aromatic acids such as, but not necessarily limited to, acetic, trifluoroacetic, propionic, n-butyric, isobutyric, valeric, caproic, pelargonic, enanthic, caprylic, lactic, acrylic, propargylic, palmitic, benzoic, phthalic, salicylic, cinnamic and naphthoic acids. With respect to phosphate compounds of the invention, the substituted phosphoric acid function can be as a free acid or preferably as a salt form. Acceptable salts of the phosphate moiety can be selected from, but not necessarily limited to, a group consisting of alkali and alkaline earths, e.g., sodium, potassium, calcium, magnesium and lithium; ammonium and substituted ammonium, including trialkylammonium, dialkylammonium and alkylammonium, e.g., triethylammonium, trimethylammonium, diethylammonium, octylammonium and cetyltrimethylammonium; and cetylpyridinium. The term lower alkyl refers to $C_1$ to $C_8$ alkyl, preferably methyl. The term aryl refers to phenyl, benzyl, or substituted phenyl or benzyl.

Preferred compounds of the invention are:

1. 5,6-dihydro-6-(3,4,6,13-tetrahydroxy-3-methyl-1,7,9,11-tridecatetraenyl)-2H-pyran-2-one [1a].
2. 5,6-dihydro-6-(3,4,6-trihydroxy-3-methyl-1,7,9,11-tridecatetraenyl)-2H-pyran-2-one [1b].
3. 5,6-dihydro-5-hydroxy-6-(3,4,6,13-tetrahydroxy-3-methyl-1,7,9,11-tridecatetraenyl)-2H-pyran-2-one [1c].
4. CL 1565-PT-3, sodium salt.
5. 4,5,8,11,13-pentahydroxy-8-methyl-9-(phosphonooxy)-2,6,12,14,16-octadecapentaenoic acid, sodium salt [2c].
6. 5,8,11,18-tetrahydroxy-8-methyl-9-(phosphonooxy)-2,6,12,14,16-octadecapentaenoic acid, sodium salt [2a].
7. 5,8,11-trihydroxy-8-methyl-9-(phosphonooxy)-2,6,12,14,16-octadecapentaenoic acid, sodium salt.
8. 6-[6,13-bis(acetyloxy)-3-hydroxy-3-methyl-4-(phosphonooxy)-1,7,9,11-tridecatetraenyl]-5,6-dihydro-2H-pyran-2-one, sodium salt.
9. 6-[6-(acetyloxy)-3-hydroxy-3-methyl-4-(phosphonooxy)-1,7,9,11-tridecatetraenyl]-5,6-dihydro-2H-pyran-2-one, sodium salt.
10. 5-(acetyloxy)-6-[6,13-bis(acetyloxy)-3-hydroxy-3-methyl-4-(phosphonooxy)-1,7,9,11-tridecatetraenyl]-5,6-dihydro-2H-pyran-2-one, sodium salt.
11. 5,6-dihydro-6-[4,6,13-tris(acetyloxy)-3-hydroxy-3-methyl-1,7,9,11-tridecatetraenyl]-2H-pyran-2-one.
12. 5,6-dihydro-6-[3,6,13-trihydroxy-3-methyl-4-(dimethylphosphonooxy)-1,7,9,11-tridecatetraenyl]-2H-pyran-2-one.

The invention in another aspect relates to a process for producing alcohols having the structural formulas 1a, 1b, and 1c, which comprises dephosphorylating pyranone phosphates having the structural formulas 3a, 3b, and 3c, respectively. The process is best carried out by reacting the pyranone phosphate with a phosphatase enzyme. The reaction is carried out in neutral or nearly neutral aqueous solution at moderate temperature, e.g., 37° C., until the reaction is complete.

The invention in another aspect relates to a process for producing phosphates having the structural formulas 2a, 2b, and 2c, which comprises hydrolyzing pyranone phosphates having the structural formulas 3a, 3b, and 3c, respectively, under ring opening conditions. The reaction can be carried out by treating the pyranone phosphate with a base such as an alkali metal hydroxide, preferably sodium hydroxide, in an aqueous medium at ambient temperature.

The invention in another aspect relates to a process for producing acyl esters of alcohols of pyranone phosphates which comprises acylating the primary and secondary hydroxyl groups of alcohols having the structural formulas 1a, 1b, and 1c, and pyranone phosphates having the structural formulas 3a, 3b, and 3c. The reaction can be carried out with a suitable acylating agent such as an acyl halide or acid anhydride, for example, p-bromobenzoyl chloride or acetic anhydride, preferably in the cold.

The invention in another aspect relates to a process for producing di- and tri-esters of phosphoric acid having the structural formulas 2a, 2b, and 2c and of pyranone phosphates having the structural formulas 3a, 3b, and 3c comprises selectively esterifying the phosphate function of said phosphates and pyranone phosphates. The reaction can be carried out in a suitable solvent such as methanol with an esterifying agent such as diazomethane in the cold.

The invention in another aspect relates to a process for producing the compound CL 1565-PT-3 comprising subjecting to chromatography a concentrate from beer containing the compound obtained by fermentation of a CL 1565-PT-3 producing strain of microorganism employing an eluent that is selective for the compound and isolating the compound from the eluate. For the process, one employs a concentrate of CL 1565-PT-3. For the chromatographic separation of CL 1565-PT-3, a system employing a reverse phase silica gel and a gradient elution using 0.05M pH 7.2 phosphate buffer-acetonitrile is preferred.

Purification of compound or products obtained by the methods of the invention is accomplished in any suitable way, preferably by column chromatography.

The invention in its composition aspect relates to pharmaceutical compositions comprising an alcohol compound having structural formula 1a, 1b, or 1c, and a pharmaceutically acceptable carrier.

The invention in another aspect relates to pharmaceutical compositions comprising a phosphate compound having the structural formula 2a, 2b, or 2c, and a pharmaceutically acceptable carrier.

The invention in another aspect relates to pharmaceutical compositions comprising a lower alkyl or aryl ester of the phosphate function of phosphates having structural formula 2a, 2b, or 2c, and further pyranone phosphate compounds having the structural formula 3a, 3b, or 3c, and a pharmaceutically acceptable carrier.

The invention in another aspect relates to pharmaceutical compositions comprising an acyl ester of an alcohol compound having structural formula 1a, 1b, or 1c, of a pyranone phosphate compound having structural formula 3a, 3b, or 3c, or a pharmaceutically acceptable salt thereof and a pharmaceutically acceptable carrier.

The invention in another aspect relates to pharmaceutical compositions comprising the compound CL 1565-PT-3 or a pharmaceutically acceptable salt thereof and a pharmaceutically acceptable carrier.

PREPARATION OF PHARMACEUTICAL COMPOSITIONS

Pyranone compounds of the invention, particularly the alcohol compound having the structural formula 1a and the compounds designated CL 1565-PT-3 and CL 1565-A diacetate in sodium salt form, have antitumor activity. The compounds are active, for example, against P388 lymphatic leukemia in vivo or L1210 mouse leukemia cells. Therefore, use of the compounds of the invention is contemplated for their antitumor activity as an active component of pharmaceutical compositions. When being utilized as cytotoxic or antileukemic agents, the compounds of the invention can be prepared and administered in various dosage forms, especially parenteral dosage forms. It will be clear to those skilled in the art that the dosage forms may comprise as the active component, one or more compounds of the invention.

The compounds are administered parenterally or intraperitoneally. Solutions of the active compound as either a salt or nonsalt form whichever is appropriate, can be prepared in an aqueous vehicle, optionally with a solubilizing agent or surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile injectable solutions or dispersions. In all cases the form must be sterile and must be fluid to the extent that easy syringeability exists. It must be stable under the conditions of manufacture and storage and must be preserved against the contamination action of microorganisms such as bacteria and fungi. The carrier can be a solvent or dispersion medium containing, for example, water, ethanol, polyol (for example, glycerol, propylene glycol, and liquid polyethylene glycol, and the like),N,N-dimethylacetamide, suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for examples, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorptions, for example, aluminum monostearate and gelatin.

Sterile injectable solutions are prepared by incorporating the active compound in the required amount in the appropriate solvent with various of the other ingredients enumerated above, as required, followed by sterilization accomplished by filtering. Generally, dispersions are prepared by incorporating the various sterilized active ingredient into a sterile vehicle which contains the basic dispersion medium and the required other ingredients from those enumerated above. In the case of the sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents, and the like. The use of such media and agents for pharmaceutically active substances is well-known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in unit dosage form for ease of administration and uniformity of dosage. Unit dosage form as used herein refers to physically discrete units suitable as unitary dosage for the mammalian subjects to be treated; each unit containing a predetermined quantity of active material calculated to produce the desired therapeutic effect in association with the required pharmaceutical carrier. The specification for the novel unit dosage forms of the invention are dictated by and directly dependent on (a) the unique characteristics of the active material and the particular therapeutic effect to be achieved, and (b) the limitation inherent in the art of compound such an active material for the treatment of disease in living subjects having a diseased codition in which bodily health is impaired as herein disclosed in detail.

The principal active ingredient is compounded for convenient and effective administration in effective amounts with a suitable pharmaceutically acceptable carrier in unit dosage form as hereinbefore disclosed. A unit dosage form can, for example, contain the principal active compound in amounts ranging from abut 10 mg to about 500 mg, with from about 25 mg to about 200 mg being preferred. Expressed in proportions, the active compound is generally present in from about 10 to about 500 mg/ml of carrier. In the case of compositions containing supplementary active ingredients, the dosages are determined by reference to the usual dose and the manner of administration of the said ingredients. The daily parenteral doses for mammalian subjects to be treated ranges from 0.01 mg/kg to 10 mg/kg. The preferred daily dosage range is 0.1 mg/kg to 1.0 mg/kg. In therapeutic use as cytotoxic or antitumor agents the compounds are administered at the initial dosage of about 0.01 mg to about 10 mg per kilogram. A dose range of about 0.1 mg to about 1.0 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The compounds of the invention are also useful as intermediates or substrates for the chemical or biochemical synthesis or in situ delivery of pharmacologically active compounds.

The invention and the best mode of practicing the same are illustrated by the following examples of preferred embodiments of selected compounds and their preparation.

EXAMPLE 1

5,6-Dihydro-6-(3,4,6,13-tetrahydroxy-3-methyl-1,7,9,11-tridecatetraenyl)-2H-pyran-2-one (CL 1565-A alcohol) [1a]

A solution of 1.4 g of the sodium salt of 5,6-dihydro-6-(3,6,13-trihydroxy-3-methyl-4-(phosphonooxy)-1,7,9,11-tridecatetraenyl)-2H-pyran-2-one, (the sodium salt of CL 1565-A [3a]) and 1.0 g of alkaline phosphatase derived from bovine (calf) intestinal mucosa (Sigma Chemical Co., St. Louis, Mo.) in 140 ml of water was incubated at 37° C. for seven hours. The reaction mixture (pH 7.2) was then lyophilized and the resulting residue was triturated with methanol. The methanol-soluble product was chromatographed on $C_8$-reverse phase silica gel. After a water wash, CL 1565-A-alcohol was eluted with water-acetonitrile (85:15). These latter fractions were combined, concentrated and lyophilized to yield 0.62 g of CL 1565-A-alcohol as a white solid. CL 1565-A-alcohol can be detected in fermentation beers by using HPLC methods patterned after the HPLC procedure described in Example 2, below.

Properties of CL 1565-A alcohol:

Ultraviolet Absorption Spectrum in Methanol: λmax 268 nm ($a_1^1$=975) with inflections at 259 and 278 nm.

Elemental Analysis:

|  | % C | % H |
|---|---|---|
| Calcd. for $C_{19}H_{26}O_6 \cdot \frac{1}{2}H_2O$: | 63.51 | 7.52 |

| -continued | | |
|---|---|---|
| | % C | % H |
| Found: | 63.41 | 7.51 |

Infrared Spectrum in $CHCl_3$:

Principal absorptions at 1720, 1600, 1285, and 1060 reciprocal centimeters.

Thin-layer Chromatography on Silica Gel-60: Solvent: chloroform-ethanol-0.5M pH 5.5 sodium acetate buffer (40:70:20), Rf: 0.8; Solvent: chloroform-isopropanol (8:2), Rf: 0.19; Solvent: chloroform-methanol-water (75:25:1), Rf: 0.60.

HPLC (see Example 2).

360 MHz Proton Magnetic Resonance Spectrum in $D_2O$ Principal Signals at: (s=singlet, d=doublet, t=triplet, m=multiplet) 1.40 s(3H), 1.47 m(1H), 1.87 m(3H), 2.52–2.71 m(2H), 3.81 dd(1H), 4.27 d(2H), 4.95 t(1H), 5.13 M(1H), 5.65 t(1H), 5.95–6.15 m(4H), 6.20 t(1H), 6.44 t(1H), 6.61 t(1H), 6.89 dd(1H), 7.15 m(1H) parts per million downfield from sodium 2,2-dimethyl-2-silapentane-5-sulfonate (DSS).

90.4 MHz 13C-Nuclear Magnetic Resonance Spectrum in $D_2O$:

| Peak Number | Chemical Shift* | Peak Number | Chemical Shift* |
|---|---|---|---|
| 1 | 24.8 | 11 | 127.0 |
| 2 | 31.9 | 12 | 128.8 |
| 3 | 41.4 | 13 | 129.8 |
| 4 | 64.9 | 14 | 133.6 |
| 5 | 67.3 | 15 | 137.3 |
| 6 | 76.4 | 16 | 137.4 |
| 7 | 77.9 | 17 | 140.4 |
| 8 | 81.5 | 18 | 151.9 |
| 9 | 122.4 | 19 | 170.5 |
| 10 | 126.8 | | |

*parts per million downfield from tetramethylsilane

Cytotoxicity Against L1210 Cells: $ID_{50}=2.5$ μg/ml.

EXAMPLE 2

5,6-Dihydro-6-(3,4,6-trihydroxy-3-methyl-1,7,9,11-tridecadetraenyl)-2H-pyran-2-one (CL 1565-B alcohol) [1b]

CL 1656-B-alcohol was prepared in a manner similar to that used for the preparation of CL 1565-A-alcohol. CL 1565-B, sodium salt (10 mg) was dissolved in 5 ml water to which 10 mg of alkaline phosphatase (CalbiochemBehring Corp., San Diego, Calif.) was added. The resulting solution was stored at 37° for 14 hours. The reaction mixture was then lyophilized and the residual solid triturated with methanol. Concentration of the methanolic solution yielded 2 mg of CL 1565-B-alcohol.

Properties of CL 1565-B alcohol:

Thin-layer Chromatography on E. Merck Silica Gel: Solvent: chloroform-isopropanol (80:20), Rf: 0.38.

High Pressure Liquid Chromatography: Column: Lichrosorb RP-8 (Brownlee Labs, Berkeley, Calif.); Solvent: water-acetonitrile (80:20); Flow-rate: 2 ml/min; Retention time: 27.0 min. Using the same HPLC conditions, the retention times of CL 1565-A-alcohol and CL 1565-B are 3.3 min and 1.0 min, respectively.

EXAMPLE 3

5,6-Dihydro-5-hydroxy-6-(3,4,6,13-tetrahydroxy-3-methyl-1,7,9,11-tridecatetraenyl)-2H-pyran-2-one (CL 1565-T alcohol) [1c]

A solution of 10 mg of CL 1565-T, sodium salt and 7.5 mg of alkaline phosphatase in 1 ml of water was stored at 37° for 18 hours. The reaction mixture was then lyophilized and the residue was triturated with ethanol. Removal of the ethanol in vacuo afforded a residue containing CL 1565-T-alcohol.

Properties of CL 1565-T alcohol:

Thin-layer Chromatography on Silica Gel GHLF: (Analtech, Inc., Neward, Del.); Solvent: chloroform-methanol-water (75:25:1); Rf: 0.44. Using the same TLC conditions, the observed Rf of CL 1565-T, sodium salt is 0.02.

EXAMPLE 4

CL 1565-PT-3, Sodium Salt

Filtered fermentation beer (719 liters) prepared from a CL 1565-PT-3 producing microorganism was passed over 31 liters of Dowex-1×2 (chloride form) packed in a 30.5 cm [O.D.] column. The effluent and the subsequent water wash did not contain any detectable amounts of the CL 1565 components. The Dowex-1 resin was then eluted with 1M sodium chloride-methanol (1:1) and the eluate was collected in two 10-liter and six 15-liter fractions. Most of the CL 1565-A, CL 1565-B, CL 1565-T, and additional minor CL 1565 components appeared in eluates two through six. These fractions were combined and diluted with 246 liters of acetone. The resulting mixture was stored at 5° C. overnight. The clear supernatant solution was removed and concentrated to 16 liters in vacuo. Lyophilization of this concentrate afforded 800 g of a solid. This product (740 g) was added to 552 g of a similar product isolated in the same manner and the combined solids were dissolved in 20 liters of water. The resulting solution (pH 6.0) was chromatographed on 50 liters of HP-20 resin contained in a 15 cm [O.D.] column. Elution of the HP-20 column with 175 liters of water removed most of the CL 1565-T and all of the minor, more polar CL 1565 components, including CL 1565-PT-3 and CL 1565-C (2c). The fractions containing these components were combined and concentrated in vacuo. The concentrate was chromatographed on 3 kg of 135 μm $C_2$-reverse phase silica gel (Merck RP-2, obtained from MCB, Inc., Indianapolis, Ind.). Elution of this column with 0.05M pH 7.2 phosphate buffer yielded a fraction that contained CL 1565-T and several minor components as determined by HPLC analysis. This fraction was concentrated and rechromatographed on 40 μm $C_8$-reverse phase silica gel (Analytichem International, Inc., Harbor City, Calif.) using a gradient elution system starting with 0.05M pH 7.2 phosphate buffer and ending with 0.05M pH 7.2 phosphate buffer-acetonitrile (95:5). Before CL 1565-T was eluted, three minor CL 1565 components were eluted in separate groups of fractions. One of these fractions contains CL 1565-C, the isolation of which is described in Example 5. The component that was eluted in the last (the third) group of these fractions is called CL 1565-PT-3. This compound was isolated by concentration of the combined CL 1565-PT-3 fractions followed by the addition of ethanol. The inorganic salts that precipitated were filtered off and the filtrate was concentrated to dryness. The residue was dissolved in ethanol and CL 1565-PT3, sodium salt was precipitated as a white solid by the addition of ethyl acetate.

Properties of CL 1565-PT-3, Sodium Salt:

Ultraviolet Absorption Spectrum in Methanol: $\lambda$max 269 nm with inflections at 259 and 278 nm.

Infrared Spectrum in KBr: principal absorptions at: 3400, 1750, 1640, 1175, 1060, and 980 reciprocal centimeters.

In Vivo Activity Against P388 Lymphatic Leukemia in Mice: dose=30 mg/kg; T/C X 100=150.

High Pressure Liquid Chromatography: Column: Chromegabond C-18, 4.6 mm I.D.×30 cm (supplied by ES Industries, Marlton, N.J.); Solvent: 0.1M pH 7.2 phosphate buffer-acetonitrile (88:12); Flowrate: 2 ml/min; Detection: ultraviolet absorption at 254 nm; Retention Time: 1.69 min.

EXAMPLE 5

4,5,8,11,18-Pentahydroxy-8-methyl-9-(phosphonooxy)-2,6,12,14,16-octadecapentaenoic acid, Sodium Salt (CL 1565-C, Sodium Salt) [2c, Sodium Salt]

The CL 1565-C containing fraction described in Example 4 was concentrated and chromatographed on 140 g of 40 $\mu$m $C_{18}$-reverse phase silica gel using 0.05M pH 7.0 phosphate buffer as the eluent. HPLC analysis of the ensuing fractions showed that CL 1565-C was rapidly eluted. The fractions that contained CL 1565-C were pooled (total volume, 220 ml), concentrated to 12 ml and rechromatographed on 140 g of $C_{18}$-reverse phase silica gel using 0.05M pH 7.1 phosphate buffer as the eluent. The eluates that contained CL 1565-C as the only UV-absorbing material were combined and lyophilized. The product (3.55 g) was dissolved in 7 ml of water and desalted on 140 g of $C_{18}$-reverse phase silica gel using water as the eluent. The fractions containing CL 1565-C were combined and lyophilized to yield CL 1565-C, sodium salt as a white solid.

Properties of CL 1565-C, Sodium Salt:

Ultraviolet Absorption Spectrum in Methanol: $\lambda$max 269 nm with inflections at 259 and 278 nm.

Infrared Spectrum in KBr: Principal absorptions at: 3400, 1560, and 1650 reciprocal centimeters.

360 MHz 1H-NMR Spectrum in $D_2O$: Principal signals at: (s=singlet, d=doublet, t=triplet, m=multiplet) 1.30 s (3H), 1.55–1.69 m (1H), 1.73 t (1H), 4.03–4.20 m (4H), 4.68 t (1H), 4.94 t (1H), 5.55 t (1H), 5.65–5.85 m (3H), 5.85–5.95 m (2H), 6.16 t (1H), 6.36 t (1H), 6.56 t (1H), and 6.76 dd (1H) parts per million downfield from DSS.

High Pressure Liquid Chromatography: Column: Chromegabond C-18, 4.6 mm I.D.×30 cm (supplied by ES Industries, Marlton, N.J.); Solvent: 0.1M pH 7.2 phosphate buffer-acetonitrile (88.12); Flowrate: 2 ml/min; Detection: ultraviolet absorption at 254 nm; Retention Time: 1.69 min. Using the same HPLC conditions, the following retention times were observed.

CL 1565-PT-3 retention time=2.20 min
CL 1565-T retention time=3.05 min
CL 1565-A retention time=4.94 min

EXAMPLE 6

Preparation of CL 1565-C, Sodium Salt, from CL 1565-T

A solution of CL 1565-T, sodium salt (22 mg) in 5 ml of water was adjusted to pH 11 with 0.1N sodium hydroxide. After two hours the pH was readjusted to pH 11 and the reaction mixture was stored overnight at 5°. The solution was adjusted to pH 7 and lyophilized to afford a white solid that contained CL 1565-C, sodium salt as shown by HPLC comparisons with a sample of CL 1565-C, sodium salt isolated using the procedure described in the previous example.

High Pressure Liquid Chromatography: Column: $\mu$Bondapak $C_{18}$-silica gel (3.9 mm I.D.×30 cm); Solvent: 0.05M pH 6.8 phosphate buffer-acetonitrile (92:8); Flowrate: 2 ml/min; Detection: ultraviolet absorption at 254 nm; Retention Time: 1.23 min. Using the same conditions, the retention times of CL 1565-C isolated in the previous example and CL 1565-T are 1.22 min and 2.30 min, respectively.

EXAMPLE 7

5,8,11,13-Tetrahydroxy-8-methyl-9-(phosphonooxy)-2,6,12,14,16-octadecapentaenoic acid, sodium salt (CL 1565-D, sodium salt) [2a, sodium salt]

CL 1565-A, sodium salt (100 mg) was dissolved in 50 ml of water. The resulting solution was adjusted to pH 11 with dilute sodium hydroxide and stored at 5° overnight. The reaction mixture (pH 8.8) was again adjusted to pH 11 and stored at 5° overnight. After adjusting to pH 6, the solution was lyophilized to yield a white solid containing CL 1565-D, sodium salt.

Properties of CL 1565-D, Sodium Salt:

Ultraviolet Spectrum in Methanol: $\lambda$max 268 nm with inflections at 259 and 278 nm.

Infrared Spectrum in KBr: Principal absorptions at: 3400, 1650, 1560, 1435, 1350, 1090, and 970 reciprocal centimeters.

High Pressure Liquid Chromatography: Column: $\mu$Bondapak $C_{18}$-silica gel (4.6 mm I.D.×30 cm); Solvent: 0.005M pH 7.3 phosphate buffer-acetonitrile (92:8); Flowrate: 2 ml/min; Detection: UV absorption at 254 nm; Retention Time: approximately 2.0 min. Using the same conditions, the retention time of CL 1565-A is approximately 4.0 min.

EXAMPLE 8

5,8,11-Trihydroxy-8-methyl-9-(phosphonooxy)-2,6,12,14,16-octadecapentaenoic acid, sodium salt (CL 1565-E, sodium salt) [2b, sodium salt]

In the same manner as Example 7 above, CL 1565-E, sodium salt, the sodium salt of 2b, can be prepared starting with CL 1565-B, sodium salt (3b, sodium salt).

EXAMPLE 9

5,8,9,11,18-Pentahydroxy-8-methyl-2,6,12,14,16-octadecapentaenoic acid, sodium salt A solution of CL 1565-A alcohol (1a, 13 mg) in 1 ml of water was adjusted to pH 10.5 with 1N sodium hydroxide. After standing for 30 minutes at room temperature, the reaction mixture (pH 8.2) was readjusted to pH 11.4 with 1N sodium hydroxide. After four hours, the solution (pH 9.2) was lyophilized to yield a solid product containing 5,8,9,11,18-pentahydroxy-8-methyl-2,6,12,14,16-octadecapentaenoic acid, sodium salt.

Properties:

Infrared Spectrum in KBr: Principal absorptions at: 3400, 2920, 1590 ($CO_2^-$), 1390, and 1060 reciprocal centimeters.

High Pressure Liquid Chromatography: Column: Whatman Partisil 10 ODS-3 (C-18 silica gel); Solvent: water-acetonitrile (8:2); Flowrate: 2 ml/min; Detection: UV absorption at 268 nm; Retention Time: 0.90 minutes. Using the same conditions, the retention time of the starting material is 3.92 minutes.

Thin-layer Chromatography on Silica Gel 60 F254 (E. Merck): Solvent: chloroform-isopropanol (8:2); Detection: inspection under ultraviolet light and by spraying with a solution of 3% ceric sulfate in 3N sulfuric acid followed by heating at 110° for ten minutes. Rf: 0.0. Using the same system, the starting material is detected at an $R_f$ of 0.2).

In the same manner, 5,8,9,11-tetrahydroxy-8-methyl-2,6,12,14,16-octadecapentaenoic acid, sodium salt and 4,5,8,9,11,18-hexahydroxy-8-methyl-2,6,12,14,16-octadecapentaenoic acid, sodium salt can be prepared starting with compound 1b and compound 1c, respectively.

EXAMPLE 10

6-[6,13-Bis(acetyloxy)-3-hydroxy-3-methyl-4-(phosphonooxy)-1,7,9,11-tridecatetraenyl]-5,6-dihydro-2H-pyran-2-one, sodium salt (CL 1565-A diacetate, sodium salt)

CL 1565-A, sodium salt (30 mg) was acetylated by treatment with acetic anhydride (0.6 ml) in the presence of pyridine (0.3 ml) for 5 hours at 5°. The volatile components were removed in vacuo and the residue was dissolved in 5% sodium bicarbonate solution and chromatographed over 20 ml of HP-20 resin. Elution with methanol-water (70:30) yielded 21 mg of CL 1565-A diacetate, sodium salt.

Properties of CL 1565-A Diacetate, Sodium Salt

Ultraviolet Absorption Spectrum in Methanol: $\lambda$max 268 nm ($a_1^1 = 650$) with inflections at 259 and 278 nm.

Thin-layer Chromatography on Silica Gel 60 F254 (E. Merck): Solvent: chloroform-isopropanol (8:2); Rf: 0.07; Solvent: chloroform-methanol-1N NH4OH (25:30:4); Rf:0.91 Using this latter solvent, the Rf of CL 1565-A, sodium salt is 0.27.

Cytotoxicity Against L1210 Cells: $ID_{50}$=approx. 6 $\mu$g/ml.

High Pressure Liquid Chromatography: Column: $\mu$Bondapak C-18 (Waters Assoc., Inc.); Solvent: 0.05M pH 6.8 phosphate buffer-acetonitrile (80:20); Flowrate: 1.5 ml/min; Retention time: 7.9 min. Using the same HPLC conditions the retention time of CL 1565-A is 2.6 min.

360 MHz Proton Magnetic Resonance Spectrum in D2O Principal signals at: (s=singlet, d=doublet, t=triplet, m=multiplet) 1.40 s (3H), 1.95 t (2H), 2.07 s (3H), 2.09 s (3H), 2.43–2.66 m (2H), 4.23 t (1H), 4.65 d (2H), 5.10 m (1H), 5.51 t (1H), 5.74 m (1H), 5.87–6.08 m (4H), 6.19 t (1H), 6.39 t (1H), 6.64 t (1H), 6.81 dd (1H), 7.10 m (1H) parts per million downfield from DSS.

EXAMPLE 11

5-(Acetyloxy)-6-[6,13-bis(acetyloxy)-3-hydroxy-3-methyl-4-(phosphonooxy)-1,7,9,11-tridecatetraenyl]5,6-dihydro-2H-pyran-2-one, sodium salt (CL 1565-T triacetate, sodium salt)

A solution of CL 1565-T, sodium salt (30 mg) in acetic anhydride (0.6 ml) and pyridine (0.3 ml) was stored at 5° for 5 hours. After the volatile components were removed in vacuo, the residue was dissolved in 5% (w/v) sodium bicarbonate and chromatographed over 20 ml of HP-20 resin. Elution with methanolwater (30:30) and concentration of the eluate in vacuo yielded 12 mg of CL 1565-T triacetate.

Properties of CL 1565-T Triacetate, Sodium Salt:

Ultraviolet Spectrum in Methanol: $\lambda$max 268 nm with inflections at 259 and 277 nm.

90 MHz Proton magnetic resonance spectrum in D2O Principal signals at: (s=singlet, d=doublet, t=triplet, m=multiplet) 1.4 s (3H), 1.5–2.1 m (2H), 2.03 s (3H), 2.05 s (3H), 2.09 s (3H), 4.05–4.45 m (1H), 4.65 d (2H), 5.15–7.2 m (12H) parts per million downfield from DSS.

Thin-layer Chromatography on Silica Gel 60 F254: Solvent: chloroform-methanol (6:4); Rf: 0.37.

In the same manner as above, 6-[6-acetyloxy-3-hydroxy-3-methyl-4-(phosphonooxy)-1,7,9,11-tridecatetraenyl]-5,6-dihydro-2H-pyran-2-one, sodium salt (CL 1565-B acetate, sodium salt) can be prepared.

EXAMPLE 12

5,6-Dihydro-6-[4,6,13-tris(acetyloxy)-3-hydroxy-3-methyl-1,7,9,11-tridecatetraenyl]-2H-pyran-2-one CL 1565-A alcohol (30 mg) was acetylated by treatment with acetic anlydride (0.6 ml) in the presence of pyridine (0.3 ml) for 5 hours at 5°. Following removal of the volatile components in vacuo, the reaction product was chromatographed on silica gel (60–200 $\mu$m), using chloroform followed by 5% methanol in chloroform. Concentration of the 5% methanol in chloroform eluate yielded CL 1565-A-alcohol triacetate (35 mg).

Properties of CL 1565-A-alcohol Triacetate:

Thin-layer Chromatography on Silica Gel 60 F254 (E. Merck): Solvent: chloroform-methanol (95:5); Rf: 0.43; Solvent: toluene-acetone (8:2); Rf: 0.21.

360 MHz Proton Magnetic Resonance Spectrum in CDCl3 Principal Signals At: (s=singlet, d=doublet, t=triplet, m=multiplet) 1.34 s (3H), 1.83–2.18 m (2H), 2.07 s (3H), 2.13 s (3H), 2.14 s (3H), 2.45–2.55 m (2H), 4.69 d (2H), 4.98–5.09 m (2H), 5.47 t (1H), 5.75 m (1H), 5.85–6.03 m (3H), 6.11 d (1H), 6.17 t (1H), 6.44 t (1H), 6.57 t (1H), 6.77 dd (1H), 6.95 m (1H) parts per million downfield from tetramethylsilane.

Chemical Ionization (CH4) Mass Spectrum:

m/z (% of base peak): 477 (M+H, 10), 459 (4), 417 (40), 399 (13), 373 (29), 357 (100), 339 (19), 313 (79), 297 (64), 279 (12), 253 (20).

EXAMPLE 13

5,6-Dihydro-6-[4,6,13-tris(4-bromobenzoyloxy)-3-hydroxy-3-methyl-1,7,9,11-tridecatetraenyl]-2H-pyran-2-one (CL 1565-A alcohol, tri-(4-bromobenzoate))

An excess of p-bromobenzoyl chloride was added to a solution of 20 mg of CL 1565-A alcohol in 1 ml of pyridine. After standing at room temperature for 48 hours, the pyridine was removed in vacuo and the residue partitioned between CH2Cl2 (10 ml) and saturated NaHCO3 (10 ml). The CH2Cl2 extract was washed with H2O (10 ml), and then evaporated to dryness. The residue was chromatographed on silica gel to give CL 1565-A-alcohol, tri-(4-bromobenzoate) (19 mg).

Properties of CL 1565-A alcohol, tri-(4-bromobenzoate):

90 MHz Proton Magnetic Resonance Spectrum in CDCl3: Principal signals at: (s=singlet, d=doublet, t=triplet, m=multiplet) 1.36 s (3H), 1.9–2.4 m (4H), 4.85 d (2H), 5.1–5.4 m (2H), 5.45–5.8 m (2H), 5.82–6.12 m (5H), 6.186.9 m (4H), 7.35–8.0 m (12H)

Thin-layer chromatography on Silica Gel: Solvent: CHCl3-isopropanol (4:1); Rf: 0.69.

EXAMPLE 14

5,6-Dihydro-6-[3,6,13-trihydroxy-3-methyl-4-(dimethylphosphonooxy)-1,7,9,11-tridecatetraenyl]-2H-pyran-2-one CL 1565-A dimethyl ester CL 1565-A, sodium salt (25 mg) was dissolved in 1 ml of methanol and added with stirring at 0° to a mixture containing 1 ml Dowex 50×2 (hydrogen form) and 15 ml methanol. A solution of diazomethane in 20 ml of ether was added immediately and, after three minutes, the yellow solution was decanted from the Dowex resin and concentrated to dryness in vacuo. The residual solid was triturated with chloroform and the chloroform-soluble material was purified by preparative layer chromatography on silica gel, using chloroform-methanol (8:2). The major UV absorbing band was removed from the silica gel plate to afford 9 mg of CL 1565-A dimethyl ester.

Properties of CL 1565-A Dimethyl Ester:

Thin-layer chromatography on Silica Gel 60 F254 (E. Merck): Solvent: chloroform-methanol (8:2); Rf: 0.49.

Ultraviolet Spectrum in Methanol: λmax 268 nm with inflections at 259 and 278 nm.

Infrared Spectrum in CHCl$_3$: Principal absorptions at: 3400, 1725, 1605, 1380, 1050, and 1020 reciprocal centimeters.

90 MHz Proton Magnetic Resonance Spectrum in CDCl$_3$ Principal Signals at: (s=singlet, d=doublet, t=triplet, m=multiplet) 1.3 s (3H), 1.55-1.85 m (2H), 2.35-2.55 m (2H), 3.78 s (3H), 3.91 s (3H), 4.23 d (2H), 4.35-5.10 m (3H), 5.5-7.0 m (10H), parts per million downfield from tetramethylsilane.

EXAMPLE 15

Preparation of Intravenous Formulations

A solution of a compound prepared by any of the above examples is prepared in 1 liter of water for injection at room temperature with stirring. The solution is sterile filtered into 500 10 ml vials, each of which contains 5 ml of solution constituted to contain 75 mg of compound and is sealed under nitrogen.

Alternatively, after sterile filtration into vials, the water may be removed by lyophilization, and the vials then sealed aseptically, to provide a powder which is redissolved prior to injection.

Preparation of Starting Materials

The pyranone phosphate starting materials for the process of the invention designated as 3a, 3b, and 3c (CL 1565-A, -B, and -T) can be made by cultivating a CL 1565 complex producing strain of a Streptomyces sp. isolate ATCC 31906 under artificial conditions and isolating the materials thus produced as described in the following Examples A, B, C, and D.

EXAMPLE A

Seed development and shake flask fermentation

The culture designated as ATCC 31906 in its dormant stage is transferred to a CIM-23 agar slant and incubated for 7–14 days at 28° C. A portion of the microbial growth from the slant is used to inoculate an 18×150 mm seed tube containing 5 ml of ARM 1550 seed medium. The seed tube is shaken at 24° C. for 3–4 days.

| CIM 23 agar slant | |
|---|---|
| Amidex corn starch | 10 g |
| N-Z amine, type A | 2 g |
| Beef Extract (Difco) | 1 g |
| Yeast Extract (Difco) | 1 g |
| Cobaltous chloride.6 H$_2$O | 0.020 g |
| Agar | 20 g |
| Distilled water | 1000 ml |
| ARM 1550 medium | % |
| Bacto-Yeast Extract (Difco) | 0.5 |
| Glucose, Monohydrate | 0.1 |
| Soluble Starch (Difco) | 2.4 |
| Bacto-Tryptone (Difco) | 0.5 |
| Bacto-Beef Extract (Difco) | 0.3 |
| CaCO$_3$ | 0.2 |

NOTE: Adjust pH to 7.5 with NaOH before adding CaCO$_3$

A portion (1 ml) of the microbial growth from the seed tube is transferred to a 300 ml Erlenmeyer baffled shake flask containing 50 ml of SM 64 production medium. The inoculated flask is incubated at 24° C. for 5 days with shaking using a gyratory shaker (2" throw) set at 180 RPM. The fermentation beer after five days of fermentation is tan in color, the mycelia are granular in appearance, and the pH of the fermentation beer is about 5.5.

| SM 64 Production Medium | |
|---|---|
| Whey (Kroger Dairy) | 35.0% by volume |
| Dextrin (Amidex B411), American Maize | 1.5% by weight |
| Pharmamedia (Traders Protein) 431307 | 1.5% by weight |
| Distilled water | |

NOTE: Adjust pH to 6.5 with sodium hydroxide

EXAMPLE B

Fermentation in 200-gallon fermentors

Seed Development

A cryogenic vial containing approximately 1 ml of culture suspension is used as the source of inoculum. The contents of this cryogenic vial are thawed and aseptically transferred to a two liter, baffled Erlenmeyer flask containing 500 ml of SD-05 seed medium. The inoculated flask is incubated for 46–48 hours at 24° C., on a gyratory shaker, at 130 RPM speed.

| SD-05 Seed Medium | % |
|---|---|
| Amberex 1003 (Amber Labs) | 0.5 |
| Glucose Monohydrate (Cerelose) | 0.1 |
| Dextrin-Amidex B411 (Corn Products) | 2.4 |
| N-Z Case (Humko Sheffield) | 0.5 |
| Spray Dried Meat Solubles (Daylin Labs) | 0.3 |
| CaCO$_3$ | 0.2 |
| Distilled water | |

After 48 hours, the contents of the seed flask are transferred aseptically to a 30-liter, stainless steel fermentor containing 16 liters of SD-05 seed medium. The inoculated fermentor is incubated for 18–24 hours at 24° C., stirred at 300 RPM, and sparged with air at 1 VVM rate. This microbial growth is used to inoculate the 200-gal production fermentor.

Production Fermentors

A 200-gal fermentor which contains 160 gal of SM 64 is sterilized by heating with steam for 40 min. at 121° C.

The medium is cooled to 24° C. and then inoculated with about 16 liters of the microbial growth from the 30-liter seed fermentor. The inoculated medium is allowed to ferment for five to seven days at 24° C., 190 RPM agitation, and sparged with 1 VVM air. Antifoam agents, Dow Corning "C" and polyglycol P-2000, are used to control foaming.

The production of CL 1565-A, CL 1565-B and CL 1565-T is monitored throughout the fermentation cycle by recording fermentation parameters such as pH and percent sedimentation or growth and by a high pressure liquid chromatographic procedure described below. An example of a fermentation profile in a 200-gal fermentor is shown in the following table.

| Fermentation Time (hr) | pH | % Sedimentation (growth) | Micrograms CL 1565-A/ml (HPLC Assay) |
|---|---|---|---|
| 0 | 6.0 | 0 | — |
| 12 | 5.8 | 3.6 | — |
| 24 | 5.1 | 13.3 | — |
| 36 | 5.15 | 14.7 | — |
| 48 | 5.35 | 19.3 | — |
| 72 | 5.45 | 22.0 | 3-6 |
| 96 | 5.95 | 24.7 | 10-20 |
| 118 | 7.65 | 43.3 | 50-65 |
| 132 | 7.80 | 39.3 | 60-65 |
| 142 | 7.90 | 40.0 | 60-70 |

This fermentor was harvested after 142 hours of fermentation with a harvest volume of 140 gal.

Isolation of CL 1565-A

EXAMPLE C

The harvested beer from the above fermentation is mixed with 34 kg of Celite 545 and filtered through a plate and frame filter press. The filtrate (473 liters) is percolated through a 30.5 cm [O.D.] column containing 120 liters of HP-20 resin (Gillies International, Inc., La Jolla, Calif.). The resin is then washed with water (605 liters), and 90:10 water:methanol (170 liters). Most of the CL 1565-A is then eluted from the resin with 80:20 water:methanol. High pressure liquid chromatographic analyses (HPLC), performed in the manner described below, of the ensuing eluates typically show the following elution profile.

| 80:20 water:methanol eluate | grams of CL 1565-A |
|---|---|
| #1 = 340 liters | <2 g |
| #2 = 340 liters | 11.5 g |
| #3 = 340 liters | 7.0 g |

Eluates #2 and #3 are separately concentrated and lyophilized to afford 90.2 g and 78.7 g, respectively, of dark brown solids. These products are combined and dissolved in 3 liters of water. The resulting solution is added to 27 liters of methanol with stirring. After standing overnight at 5° C., the mixture is filtered and the precipitate is washed with 5 liters of methanol. The filtrate and wash are combined, concentrated in vacuo, and lyophilized to yield 104.5 g of a solid. A portion of this product (95 grams) in 1.5 liters of water is added slowly with mixing to 17 liters of 1-propanol. After one hour the resulting mixture is filtered and the precipitate is washed with 2 liters of 1-propanol. The filtrate and wash are combined, concentrated, and lyophilized to afford 57 g of a solid which, by HPLC analysis, typically contains about 15 g of CL 1565-A.

This product is chromatographed, in approximately 15 g lots, on 1.2 liters of 40 $\mu$m $C_{18}$-silica gel (Analytichem International, Inc., Harbor City, Calif.) contained in a 7.6 cm [O.D.] column. The eluent is 0.005 M pH 4.5 ammonium acetate buffer followed by 0.005 M pH 4.5 ammonium acetate containing 5% acetonitrile. The fractions collected are assayed by HPLC. The fractions containing CL 1565-A are 30 pooled, concentrated, and lyophilized. A portion (570 mg) of the resulting product is rechromatographed using a Prep LC/System 500 apparatus fitted with a Prep-Pak TM -500/$C_{18}$ column (Waters Instruments, Inc., Milford, Mass.) and 0.1 M pH 6.5 phosphate buffer containing 10% acetonitrile as the eluent. The major fractions, containing approximately 375 mg of CL 1565-A, are pooled and concentrated in vacuo. The aqueous solution is passed through a column containing 200 ml of HP-20 resin packed in water. The resin is then washed with 1400 ml of water and CL 1565-A 5 remaining on the column is eluted with 350 ml of 50% methanol. The eluate is concentrated in vacuo and passed through a column containing 35 ml of Dowex-50x2 ($Na^+$). The effluent (pH 5.5) and a water wash of the resin are combined and lyophilized to yield 180 mg of purified CL 1565-A, isolated as a sodium salt.

Analysis of this product shows typically that the product contains approximately 1.3 moles of sodium per 1.0 mole of parent CL 1565-A free acid. Because the free acids (CL 1565-A, CL 1565-B, and CL 1565-T) are labile, they preferably are isolated in the salt form such as the sodium salt form, preferably as the salts having about 1.0 to about 2.0 moles of sodium per 1.0 mole of free acid.

EXAMPLE D

Filtered beer (719 liters), prepared in the same manner as described above, are passed over 31 liters of Dowex-1×2 (chloride form) packed in a 30.5 cm [O.D.] column. The effluent and the subsequent water wash usually do not contain any detectable amounts of the CL 1565 components. The entire fractionation described herein is monitored by the HPLC method described below using 0.1M pH 6.8 phosphate buffer ($Na^+$)-acetonitrile (88:12) as the solvent system. The Dowex-1 resin is then eluted with 1M sodium chloride-methanol (1:1) and the eluate is collected in two 10-liter and six 15-liter fractions. The CL 1565-A, CL 1565-B, CL 1565-T appear in eluates two through six. These fractions are combined and diluted with 246 liters of acetone. The resulting mixture is stored at 5° C. overnight. The clear supernatant solution is removed and concentrated to 16 liters in vacuo. Lyophilization of this concentrate affords about 800 g of a solid. This product (740 g) is added to about 550 g of a similar product isolated in the same manner and the combined solids are dissolved in 20 liters of water. the resulting solution (pH 6.0) is chromatographed on 50 liters of HP-20 resin contained in a 15 cm [O.D.] column. Elution of the HP-20 column with 175 liters of water removes most of the CL 1565-T. Most of the CL 1565-A component is eluted with 100 liters of methanol-water (15:85); CL 1565-B and the remaining amount of CL 1565-A are eluted with 83 liters of methanol-water (50:50). The eluates richest in CL 1565-A are combined, concentrated, and lyophilized to afford a solid which, by HPLC analysis, contains about 110 g of CL 1565-A.

A 75-gram portion of this product is dissolved in two liters of 0.05M pH 6.8 phosphate buffer and further purified by chromatography on 52 liters (25 kg) of 100 μm C$_{18}$ reverse phase silica gel (Analytichem International, Inc., Harbor City, Calif.) packed in 0.05M pH 6.8 phosphate buffer (Na$^+$) in a 15 cm [O.D.] column. The column is developed with 0.05M phosphate buffer containing increasing amounts (4.0–6.5%) of acetonitrile. The early fractions contain CL 1565-T. CL 1565-a is eluted in subsequent fractions. The fractions containing CL 1565-A as the only UV-absorbing component are pooled and concentrated in vacuo to 20 liters. This concentrate is stored overnight at 5° C. and the inorganic salt that precipitates is filtered off. The filtrate is then charged on a 15 cm [O.D.] column containing 28 liters of HP-20 resin. The resin is washed with water (66 liters), and CL 1565-A is then eluted with 42 liters of methanol-water (50:50). The eluates that contain the majority of the CL 1565-A are combined (26 liters), concentrated, and lyophilized to yield CL 1565-A containing some inorganic impurities. The inorganic impurities can be removed by dissolving the product in methanol (at 50 to 100 mg/ml), filtering off any insoluble material, and converting the filtrate to an aqueous solution by continually adding water to the filtrate as it is being concentrated in vacuo. Final purification of CL 1565-A is effected by chromatography of the resulting aqueous concentrate on HP-20 resin.

Properties of CL 1565-A, Sodium Salt:

Ultraviolet Absorption Spectrum in MeOH: λmax 268 nm ($a_1^1$=805) with inflections at 259 and 278 nm.

Infrared Absorption Spectrum in KBr: Principal absorptions at: 3400, 1710, 1630, 1420, 1387, 1260, 1155, 1090, 1060, 975, 920, 820, and 775 reciprocal centimeters.

Optical Rotation: $[\alpha]_D^{23}$ +28.2° (1.0% in 0.1M pH 7 phosphate buffer).

Elemental Analysis:

|  | % C | % H | % Na | % P |
|---|---|---|---|---|
| Calcd. for C$_{19}$H$_{27.7}$O$_{10}$Na$_{1.3}$P: | 47.84 | 5.86 | 6.27 | 6.49 |
| Found: | 48.01 | 5.88 | 6.05 | 6.3 |

Mass Spectrum (via fast atom bombardment): Calcd. for [C$_{19}$H$_{25}$Na$_2$O$_9$P+H]$^+$=m/z 475; [C$_{19}$H$_{26}$Na O$_9$P+H]$^+$=m/z 453; Found: m/z 475, 453.

360 MHz Proton Magnetic Resonance Spectrum in D$_2$O: Principal signals at: (s=singlet, d=doublet, t=triplet, m=miltiplet) 1.29s (3H), 1.58t (1H), 1.70m (1H), 2.49–2.58 m (2H), 4.13–4.18 m (3H), 4.86 t (1H), 5.09 m (1H), 5.53 t (1H), 5.9–6.0 m (4H), 6.14 t (1H), 6.32 t (1H), 6.55 t (1H), 6.75 dd (1H), and 7.09 m (1H) parts per million downfield from sodium 2,2-dimethyl-2-silapentane-5-sulfonate (DSS).

$^{13}$C-Nuclear Magnetic Resonance Spectrum in D$_2$O:

| Principal signals at: | |
|---|---|
| peak number | peak number |
| 1 | 168.4 |
| 2 | 149.8 |
| 3 | 138.1 |
| 4 | 135.0 |
| 5 | 134.4 |
| 6 | 131.3 |
| 7 | 127.4 |
| 8 | 126.7 |
| 12 | 79.5 |
| 13 | 79.0 |
| 14 | 75.6 |
| 15 | 64.4 |
| 16 | 62.7 |
| 17 | 39.4 |
| 18 | 29.7 |
| 19 | 23.5 parts per million |

-continued

| Principal signals at: | | |
|---|---|---|
| peak number | peak number | |
| 9 | 124.9 | downfield from |
| 10 | 124.8 | tetramethylsilane |
| 11 | 120.1 | (TMS). |

The $^{31}$P-Nuclear Magnetic Resonance Spectrum in D$_2$O exhibits a doublet (J=10 Hz) at 0.504 ppm downfield from 85% phosphoric acid.

High Pressure Liquid Chromatography: Column: μBondapak ™ C$_{18}$ silica gel (3.9 mm I.D. ×30 cm); Solvent: 0.005M pH 7.3 sodium phosphate buffer-acetonitrile (90:10); Flowrate: 2 ml/min; Detection: ultraviolet absorption at 254 nm; Retention time: 2.8 min.

Isolation of Additional CL 1565 Components

Careful chromatography of the concentrates obtained from CL 1565 beers on C$_{18}$-silica gel or HP-20 resin affords fractions that contain CL 1565 components other than CL 1565-A. CL 1565-B and CL 1565-T are isolated as essentially pure compounds. CL 1565 components A, B, and T can be readily distinguished by HPLC on a μBondapak ™ C$_{18}$-silica gel column (3.9 mm I.D. ×30 cm) using 0.05M–0.10M phosphate buffers containing varying proportions of acetonitrile at a flowrate of 1.5 ml/min and detection by ultraviolet absorption at 254 nm. Typical retention times of CL 1565-A, B, and T using the above HPLC conditions are given in the following table.

| | Retention time (min) in: | |
|---|---|---|
| | Solvent A* | Solvent B** |
| CL 1565-T | 2.8 | <1.5 |
| CL 1565-A | 4.3 | <1.5 |
| CL 1565-B | >15 | 4.2 |

*0.05 M pH 7.4 phosphate buffer-acetonitrile (87:13)
**0.05 M pH 7.4 phosphate buffer-acetonitrile (78:22)

Crude beers can be assayed in the above manner except the solvent used is 0.1M pH 6.8 phosphate buffer-acetonitrile (88:12). In this case, at a flowrate of 2 ml/min, the retention times of CL 1565-T, CL 1565-A, and CL 1565-B are approximately 2.7, 5.0, and >12 minutes, respectively.

CL 1565-T is eluted earlier than CL 1565-A from HP-20 resin and from reverse phase silica gel. It can be isolated from the early fractions of the C$_{18}$-silica gel column described in example D, above, using HP-20 resin. CL 1565-B is eluted more slowly than CL 1565-A from HP-20 resin and from reverse phase silica gel. CL 1565-b is eluted with 50% methanol during the HP-20 chromatography of the crude Dowex-1 product described in example D, above. This component can best be isolated by rechromatography on HP-20 followed by chromatography on 40 μm C$_{18}$-silica gel using essentially the same procedure described for the purification of CL 1565-A.

Properties of CL 1565-T, Sodium Salt:

Ultraviolet Absorption Spectrum in MeOH: Nearly identical to that for CL 1565-A, sodium salt, with $a_1^1$=774 at λmax 268 nm and inflections at 260 and 278 nm.

Infrared Absorption Spectrum in KBr: Principal absorptions at: 3400, 1715, 1630, 1380, 1260, 1090, 970, 830 and 770 reciprocal centimeters.

Mass Spectrum (via fast atom bombardment): Calcd. for $[C_{19}H_{25}Na_2O_{10}P+H]^+ = m/z$ 491; Found: m/z 491.

360 MHz Proton Magnetic Resonance Spectrum in $D_2O$: The $^1$H-NMR spectrum of CL 1565-T is very similar to the $^1$NMR spectrum of CL 1565-A with the exception that the former spectrum wxhibits a characteristic one proton signal appearing as a doublet of doublets at 4.34 ppm and is devoid of any signals between 2.2–3.2 ppm downfield from DSS. Principal Signals of CL 1565-T, sodium salt are at: (s=singlet, d=doublet, t=triplet, m=multiplet) 1.30 s (3H), 1.55–1.64 m (1H), 1.73 t (1H), 4.13–4.20 m (1H), 4.16 d (2H), 4.34 dd (1H), 4.94 t (1H), 5.09 dd (1H), 5.55 t (1H), 5.89–6.06 m (3H), 6.16 m (2H), 6.36 t (1H), 6.56 t (1H), 6.76 dd (1H), 7.14 dd (1H ) parts per million downfield from DSS.

90.4 MHz $^{13}$C-Nuclear Magnetic Resonance Spectrum in $D_2O$:

| Peak Number | Chemical Shift* | Peak Number | Chemical Shift* |
|---|---|---|---|
| 1 | 24.10 | 11 | 126.91 |
| 2 | 41.60 | 12 | 127.18 |
| 3 | 64.68 | 13 | 128.99 |
| 4 | 64.90 | 14 | 133.36 |
| 5 | 66.67 | 15 | 136.87 |
| 6 | 78.28 | 16 | 137.23 |
| 7 | 79.81 | 17 | 142.27 |
| 8 | 84.33 | 18 | 149.46 |
| 9 | 124.40 | 19 | 169.66 |
| 10 | 126.21 | | |

*parts per million downfield from TMS

Properties of CL 1565-B, Sodium Salt:

Ultraviolet Absorption Spectrum in MeOH: $\lambda$max 267 nm ($a_1^1$=805) with inflections at 259 and 277 nm.

Infrared Absorption Spectrum in KBr: Principal Absorptions at: 1720, 1640, 1385, 1200, 1060, 970, and 820 reciprocal centimeters.

360 MHz Proton Magnetic Resonance Spectrum in $D_2O$: Principal Signals at: (s=singlet, d=doublet, t=triplet, M=multiplet) 1.32 s (3H), 1.58 t (1H), 1.72 t (1H), 1.79 d (3H), 2.45–2.68 m (2H), 4.15 t (1H), 4.89 t (1H), 5.10 m (1H), 5.49 t (1H), 5.83–6.21 m (6H), 6.50–6.64 m (2H), 7.06–7.13 m (1H) parts per million downfield from DSS.

90.4 MHz $^{13}$C-Nuclear Magnetic Resonance Spectrum in $D_2O$:

| Peak Number | Chemical Shift* | Peak Number | Chemical Shift* |
|---|---|---|---|
| 1 | 20.70 | 11 | 127.24 |
| 2 | 25.06 | 12 | 129.47 |
| 3 | 31.91 | 13 | 129.90 |
| 4 | 41.85 | 14 | 134.66 |
| 5 | 66.85 | 15 | 135.94 |
| 6 | 77.87 | 16 | 136.67 |
| 7 | 80.87 | 17 | 140.42 |
| 8 | 81.64 | 18 | 152.01 |
| 9 | 122.41 | 19 | 170.56 |
| 10 | 124.45 | | |

*parts per million downfield from TMS

Having thus described our invention, what we claim and desire by Letters Patent to secure are the following:

We claim:

1. A compound having the name 5,6-dihydro-6-(3,4,6,13-tetrahydroxy-3-methyl-1,7,9,11-tridecatetraenyl)-2H-pyran-2-one.

2. A compound having the name 5,6-dihydro-6-(3,4,6-trihydroxy-3-methyl-1,7,9,11-tridecatetraenyl)-2H-pyran-2-one.

3. A compound having the name 5,6-dihydro-5-hydroxy-6-(3,4,6,13-tetrahydroxy-3-methyltrideca-tetraenyl-2H-pyran-2-one.

* * * * *